United States Patent [19]

Fudono et al.

[11] Patent Number: 4,998,582
[45] Date of Patent: Mar. 12, 1991

[54] REFRIGERATOR SYSTEM FOR A CONTAINER

[75] Inventors: Kanji Fudono; Hiroshi Ogawa; Toshimasa Takahashi, all of Nagoya; Toshio Yamashita, Nishi-Biwajima, all of Japan

[73] Assignee: Mitsubishi Jukogyo Kabushiki Kaisha, Tokyo, Japan

[21] Appl. No.: 454,505

[22] Filed: Dec. 21, 1989

[30] Foreign Application Priority Data

Mar. 6, 1989 [JP] Japan ................................. 1-24779

[51] Int. Cl.$^5$ ...................... F25B 29/00; G05D 23/00
[52] U.S. Cl. .................................. 165/11.1; 236/94; 165/28; 165/12; 374/4; 374/43
[58] Field of Search ............... 165/11.1, 28, 12; 236/94; 374/4, 5, 43, 44

[56] References Cited

U.S. PATENT DOCUMENTS

| | | | |
|---|---|---|---|
| 4,024,751 | 5/1977 | Potrzebowski | 374/43 |
| 4,236,403 | 12/1980 | Poppendick | 374/44 |
| 4,237,732 | 12/1980 | Grein et al. | 374/4 |
| 4,246,785 | 1/1981 | Sellers et al. | 374/43 |
| 4,296,627 | 10/1981 | Lindstrom | 165/11.1 |
| 4,381,549 | 4/1983 | Stamp, Jr. et al. | 165/11.1 |
| 4,574,871 | 3/1986 | Parkinson et al. | 236/94 |
| 4,647,221 | 3/1987 | Szabo | 374/44 |

FOREIGN PATENT DOCUMENTS

| | | | |
|---|---|---|---|
| 0052347 | 3/1987 | Japan | 236/94 |
| 0080443 | 4/1987 | Japan | 236/94 |

*Primary Examiner*—John Ford
*Attorney, Agent, or Firm*—Wenderoth, Lind & Ponack

[57] ABSTRACT

A known refrigerating system for a container is improved to include container wrong or abnormal condition diagnostic facilities. Such additional facilities include a container inside temperature detector, a container outside temperature detector, a control responsive to a wrong condition diagnosis instruction for operating an evaporator fan and an electric heater of the refrigerating system, and a wrong condition diagnostic device for diagnosing whether or not a wrong condition of the container is present on the basis of the temperatures detected by the respective temperature detectors after a predetermined period of operation of the evaporator fan and the electric heater. If the temperature detected by the container inside temperature detector has risen to a predetermined temperature or higher in relation to the temperature detected by the container outside temperature detector, the wrong condition diagnostic device diagnoses that the container is normal, but if the temperature has not risen to the predetermined temperature, the container is diagnosed to be abnormal.

10 Claims, 3 Drawing Sheets

REFRIGERATOR SYSTEM FOR A CONTAINER

BACKGROUND OF THE INVENTION

1. Field of the Invention:

The present invention relates to a refrigerator system for a container.

2. Description of the Prior Art:

A known refrigerator system for a container in the prior art is illustrated in block diagram form in FIG. 4, and an arrangement of the same system within a container is shown in FIG. 5. In these figures, reference numeral 1 designates a container or enclosed space, numeral 2 designates a compressor, numeral 3 designates a condenser, numeral 4 designates an electronic expansion valve, numeral 5 designates an evaporator, numeral 6 designates a hot gas modulating valve, numeral 7 designates a condenser fan, numeral 8 designates an evaporator fan, numeral 9 designates a container outside temperature detector, numeral 10 designates a container inside temperature detector, numeral 11 designates an electric heater, and numeral 12 designates a controller. Solid line arrows in FIG. 4 indicate the direction of flow of a coolant, and dotted line arrows indicate the direction of flow of air.

In the above-described system, a coolant compressed by the compressor 2 enters the condensor 3, where it is cooled by heat-exchange with air caused to flow by the condenser fan 7, and becomes a high-pressure liquid coolant. The coolant is reduced in pressure in the electronic expansion valve 4, and then enters the evaporator 5, where it is heated by heat-exchange with air caused to flow by the evaporator fan 8, and it becomes a low-pressure gas coolant and returns to the compressor 2. The above-mentioned is a basic operation of a refrigerating system, and in this system the controller 12 compares the temperature detected by the temperature detector 10 within the container 1 with a preset temperature within the container 1, and according to the results of such comparison it performs adjustment of an extent of opening of the hot gas modulating valve 6, ON-OFF switching of the electric heater 11 or adjustment of an extent of opening of the electronic expansion valve 4, and thereby serves to maintain the temperature within the container 1 constant.

However, in the case where the container 1 has superannuated or has been damaged or defective due to any cause, the thermal insulation property of the container is degraded, resulting in large leakage of heat, and a preset temperature within the container cannot be attained, so that a wrong or abnormal condition for the load in the container is produced. Also, even if the preset temperature within the container were to be attained, there would occur a wrong condition in that it takes a long time until the set temperature is attained or a heavy load is applied to the refrigerating system. Moreover, when such a wrong condition had occurred, in the prior art it was not known whether the problem involved the refrigerator system or the problem involved the container.

SUMMARY OF THE INVENTION

It is therefore one object of the present invention to provide a novel refrigerator system for an enclosed space such as a container associated with a container wrong condition diagnostic capability, in which a capability of diagnosing a wrong condition of the container is imported to the controller in the refrigerating system, which originally serves to control the refrigerator system so that during use of the container the temperature within the container may be maintained constant, and prior to use of the container, the existence of a wrong or abnormal or defective condition of the container can be discovered by operating the system in part.

According to one feature of the present invention, there is provided a refrigerating system for a container including an evaporator, an evaporator fan and an electric heater disposed inside of the container, which system comprises container wrong condition diagnostic facilities including a container inside temperature detector, a container outside temperature detector, control means responsive to a wrong condition diagnosis instruction or signal for operating the evaporator fan and the electric heater, and wrong condition diagnostic means for diagnosing whether or not a wrong condition of the container is present on the basis of the temperatures detected by the respective temperature detectors after a predetermined period of operations of the evaporator fan and the electric heater.

According to another feature of the present invention, there is provided the above-featured refrigerating system for a container, in which the wrong condition diagnostic means diagnoses a normal condition if the temperature detected by the container inside temperature detector has risen to a predetermined temperature or higher in relation to the temperature detected by the container outside temperature detector, but an abnormal condition if such inside temperature has not risen to the predetermined temperature.

According to still another feature of the present invention, there is provided the above-featured refrigerating system for a container, which further comprises message display means for displaying the results of the diagnosis by the wrong condition diagnostic means.

If the container wrong condition diagnostic facilities in the refrigerating system according to the present invention are operated when the container is in an empty condition, the control means in the system starts operation of the evaporator fan and the electric heater while the inherent refrigerating function is maintained interrupted. Thereby the inside of the container is heated. After a predetermined period of time has elapsed, the temperatures on the inside and on the outside of the container detected by the respective temperature detectors are investigated automatically with reference to a known correlation between the temperatures on the inside and on the outside of a normal container, and in the event that the temperature on the inside of the container has not risen to a predetermined temperature, it is automatically determined that leakage of heat exists. In this way, the presence or absence of a wrong or abnormal condition can be automatically diagnosed.

Therefore, according to the present invention, prior to practical use of a refrigerating container, it can be automatically and easily diagnosed whether or not there exists a wrong or abnormal or defective condition of the container rather than of the refrigerating facility itself.

The above-mentioned and other objects, features and advantages of the present invention will become more apparent by reference to the following description of preferred embodiment of the invention taken in conjunction with the accompanying drawings.

DESCRIPTION OF THE PREFERRED EMBODIMENTS

Figure 1:
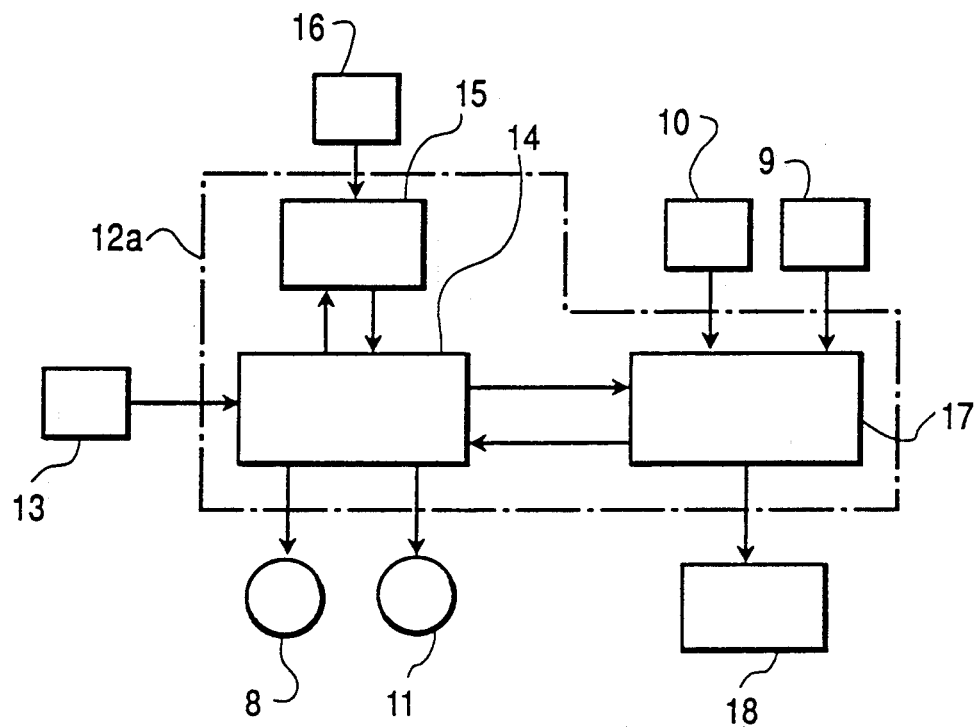
FIG. 1 is a block diagram of one preferred embodiment of the present invention.
Figure 4:
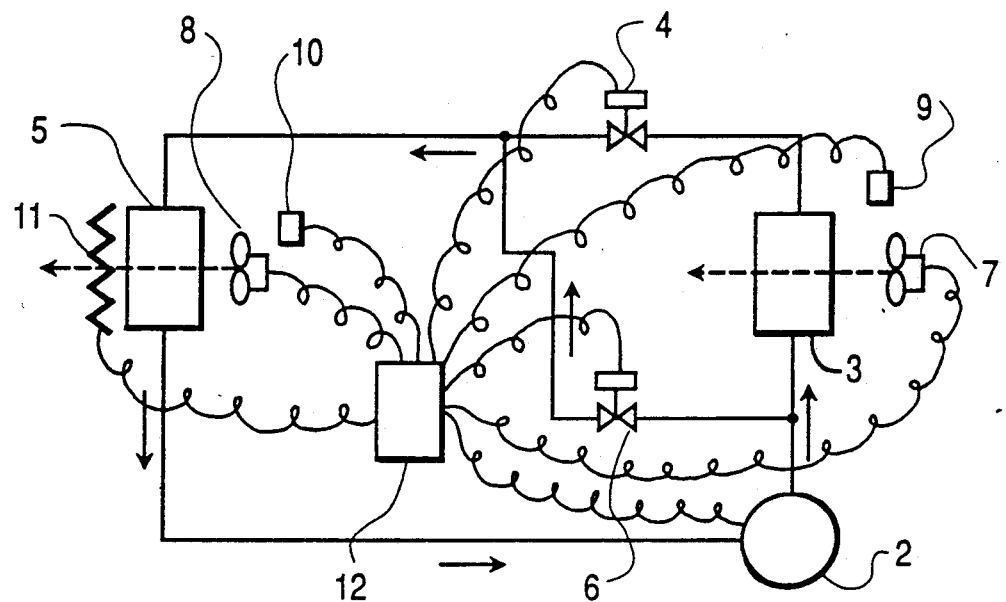
FIG. 4 is a block diagram of a refrigerating system for a container in the prior art.
Figure 5:
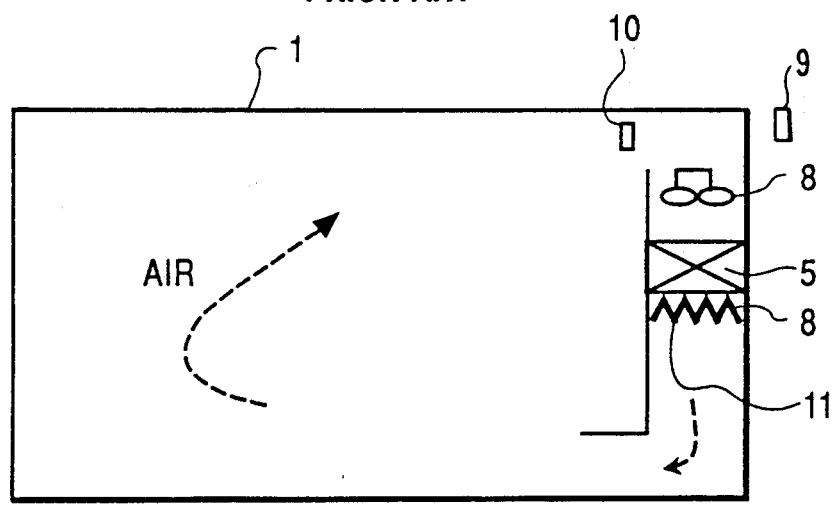
FIG. 5 is a schematic view showing arrangement of a refrigerating system for a container in the prior art.

One preferred embodiment of a refrigerating system for a container according to the present invention, which comprises container wrong condition diagnostic facilities, is illustrated in blocks in FIG. 1. These facilities consist of a portion included in the refrigerating system in the prior art, and a newly added portion, and these respective portions cooperate to achieve the desired object. In FIG. 1, the region encircled by a dash-dot line 12a is a portion provided in the controller 12 of the system in the prior art such as shown in FIG. 4. With regard to the portions other than the illustrated portion, the refrigerating system in the prior art as shown in FIGS. 4 and 5 can be used in itself. In FIG. 1, reference numeral 8 designates an evaporator fan, numeral 9 designates a container outside temperature detector, numeral 10 designates a container inside temperature detector, numeral 11 designates an electric heater, numeral 13 designates a wrong condition diagnostic switch, numeral 14 designates control means, numeral 15 designates a timer, numeral 16 designates timer setting means, numeral 17 designates wrong condition diagnostic means, and numeral 18 designates message display means. In addition, arrows in this figure represent the direction of transmission of informations or instructions.

Figure 2:
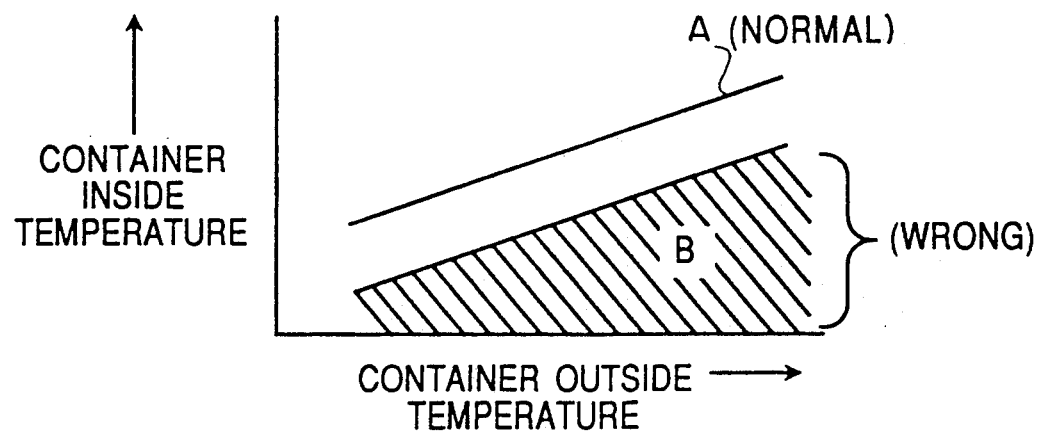
FIG. 2 is a diagram showing the relation between a container inside temperature and a container outside temperature to be referred to for explaining the principle of the present invention.

Now, a principle of the present invention will be explained with reference to FIG. 2, in which the temperature on the inside of the container is indicated as the ordinate, and the temperature on the outside of the container is indicated as the abscissa. Since heat generating rates of the evaporator fan motor and the electric heater as well as the rate of leakage of heat from a normal container are respectively constant, when the inside of the container has been heated for a certain period of time by operating the evaporator fan motor and the electric heater under the condition where a load is not present in the container, in the case of a normal container the relation between the temperatures on the inside and on the outside of the container would be the relation represented by line A in FIG. 2. In the ca of a wrong container having a large rate of leakage of heat, since the temperature on the inside of the container does not rise much, the relation of the temperatures on the inside and on the outside of the container will fall in the hatched region B in FIG. 2. In this way, a wrong condition of a container can be discovered by measuring the temperatures on the inside and on the outside of the container after the evaporator fan and the electric heater have been operated for a certain period of time, and investigating the measured temperatures with reference to the known data of the temperature relation as shown in FIG. 2.

Figure 3:
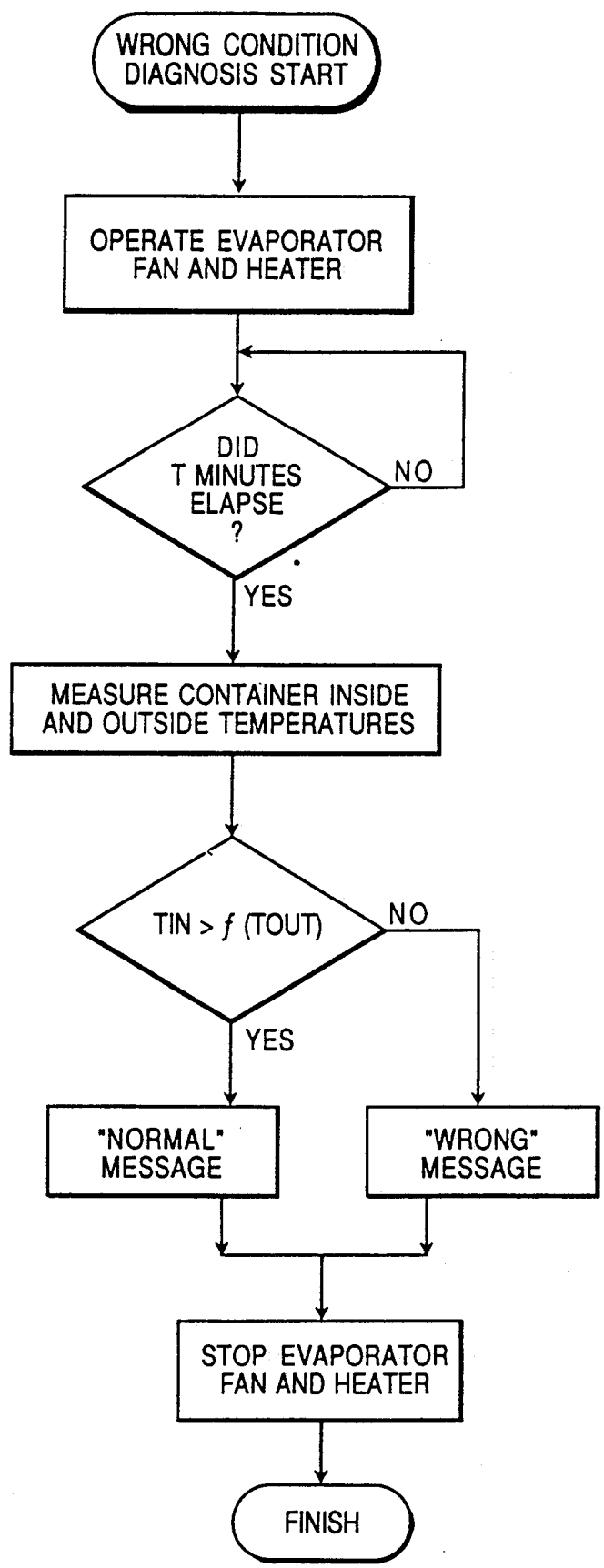
FIG. 3 is a flow chart of the operation of the illustrated embodiment.

Next, the operation of the illustrated embodiment of the present invention will be explained on the basis of the above-described construction and operation principle. Under the condition where a container 1 having the construction such as shown in FIG. 5 is held empty, the wrong condition diagnostic switch 13 in FIG. 1 is actuated to start wrong condition diagnosis. At this moment, the control means 14 starts operations of the evaporator fan 8 and the electric heater 11 while the inherent refrigerating function is maintained interrupted, and thereby the inside of the container is heated up. At the same time, the timer 15 starts counting, and after a time preset by the timer setting means 16 has elapsed, in response to an instruction issued from the control means 14, the wrong condition diagnostic means 17 compares the temperatures detected by the container inside temperature detector 10 and the container outside temperature detector 9, respectively, and if the container inside temperature ($T_{in}$) has risen to a predetermined temperature or higher in relation to the container outside temperature ($T_{out}$), then it is diagnosed that the container is normal, but if the container inside temperature ($T_{in}$) has not risen up to that predetermined temperature, it is diagnosed that leakage of heat is present, and it is displayed by the message display means 18. When the above-mentioned diagnosis has finished, the control means 14 stops the evaporator fan 8 and the electric heater 11. The abovementioned process is represented by the flow chart in FIG. 3.

As described in detail above, since the refrigerating system for a container according to the present invention is associated with container wrong condition diagnostic facilities, the refrigerating system per se can, diagnose either the presence or absence of leakage of heat from the container, that is, either the presence or absence of a wrong condition of the container.

Since the refrigerating system for a container according to the present invention is provided with container wrong condition diagnostic facilities including of a container inside temperature detector, a container outside temperature detector, control means responsive to a wrong condition diagnosis instruction for operating the evaporator fan and the electric heater, and wrong condition diagnostic means for diagnosing whether or not a wrong condition of the container is present on the basis of the temperatures detected by the respective temperature detectors after a predetermined period of operation of the evaporator fan and the electric fan, by operating this refrigerating system in part when the container is empty, either presence or absence of leakage of heat, that is, a wrong condition of the container can be diagnosed.

While a principle of the present invention has been described above in connection to one preferred embodiment of the invention, it is a matter of course that many apparently widely different embodiments of the present invention could be made without departing from the spirit of the present invention.

What is claimed is:

1. In a refrigerating system for a container, said refrigerating system including an evaporator, an evaporator fan and an electric heater to be disposed inside the container, the improvement comprising means operable in association with said refrigerating system for determining the existence of an abnormal condition of the container, said determining means comprising:

a container inside temperature detector to be located inside the container for detecting the temperature therein;

a container outside temperature detector to be located outside the container for detecting the temperature outwardly thereof;

control means, operably connected to said evaporator fan and to said electric heater, and operable in response to an abnormal condition diagnosis instruction, for operating said evaporator fan and said electric heater, whereby the temperature inside the container increases; and abnormal condition diagnostic means, operably connected to said container inside temperature detector and to said container outside temperature detector, for diagnosing whether or not an abnormal condition of the container is present as a function of the temperatures detected by said container inside temperature detector and said container outside temperature detector after a predetermined period of time of operation of said evaporator fan and said electric heater by said control means.

2. The improvement claimed in claim 1, wherein said abnormal condition diagnostic means is operable to diagnose a normal condition of the container if the temperature detected by said container inside temperature detector has risen at least to a predetermined temperature relative to the temperature detected by said container outside temperature detector after said predetermined period of time, and is operable to diagnose an abnormal condition of the container if the temperature detected by said container inside temperature detector has not risen to said predetermined temperature after said predetermined period of time.

3. The improvement claimed in claim 2, further comprising means, operatively connected to said abnormal condition diagnostic means, for displaying the results of the diagnosis thereby.

4. The improvement claimed in claim 1, further comprising means, operatively connected to said abnormal condition diagnostic means, for displaying the results of the diagnosis thereby.

5. The improvement claimed in claim 1, wherein said refrigerating system further includes compressor, condenser and other conventional components that are operatively connected to said control means so that their operation is maintained interrupted thereby during diagnosing operation by said abnormal condition diagnostic means.

6. A diagnosing assembly, for use with a refrigerating system for a container, for determining the existence of an abnormal condition of the container, said assembly comprising:

a container inside temperature detector to be located inside a container for detecting the temperature therein;

a container outside temperature detector to be located outside the container for detecting the temperature outwardly thereof;

control means, to be operably connected to an evaporator fan and to an electric heater of the refrigerating system, and operable in response to an abnormal condition diagnosis instruction, for operating the evaporator fan and the electric heater, whereby the temperature inside the container increases; and abnormal condition diagnostic means, operably connected to said container inside temperature detector and to said container outside temperature detector, for diagnosing whether or not an abnormal condition of the container is present as a function of the temperatures detected by said container inside temperature detector and said container outside temperature detector after a predetermined period of time of operation of the evaporator fan and the electric heater by said control means.

7. An assembly as claimed in claim 6, wherein said abnormal condition diagnostic means is operable to diagnose a normal condition of the container if the temperature detected by said container inside temperature detector has risen at least to a predetermined temperature relative to the temperature detected by said container outside temperature detector after said predetermined period of time, and is operable to diagnose an abnormal condition of the container if the temperature detected by said container inside temperature detector has not risen to said predetermined temperature after said predetermined period of time.

8. An assembly as claimed in claim 7, further comprising means, operatively connected to said abnormal condition diagnostic means, for displaying the results of the diagnosis thereby.

9. An assembly as claimed in claim 6, further comprising means, operatively connected to said abnormal condition diagnostic means, for displaying the results of the diagnosis thereby.

10. An assembly as claimed in claim 6, wherein said control means is adapted to be operatively connected to a compressor, a condenser and other conventional components of the refrigerating system such that their operation is maintained interrupted by said control means during diagnosing operation by said abnormal condition diagnostic means.

* * * * *